United States Patent
O'Sullivan et al.

(10) Patent No.: US 9,288,368 B2
(45) Date of Patent: Mar. 15, 2016

(54) VIDEO AND MAP DATA SYNCHRONIZATION FOR SIMULATED ATHLETIC TRAINING

(71) Applicant: Delightfit, Inc., Carlsbad, CA (US)

(72) Inventors: Peter O'Sullivan, San Marcos, CA (US); Richard M. Yumul, Chula Vista, CA (US)

(73) Assignee: DELIGHTFIT, INC., Carlsbad, CA (US)

( * ) Notice: Subject to any disclaimer, the term of this patent is extended or adjusted under 35 U.S.C. 154(b) by 112 days.

(21) Appl. No.: 14/048,634

(22) Filed: Oct. 8, 2013

(65) Prior Publication Data
US 2015/0098021 A1   Apr. 9, 2015

(51) Int. Cl.
| | |
|---|---|
| H04N 5/04 | (2006.01) |
| A63B 24/00 | (2006.01) |
| H04N 21/236 | (2011.01) |
| H04N 21/242 | (2011.01) |
| H04N 21/4223 | (2011.01) |
| H04N 21/43 | (2011.01) |
| H04N 21/45 | (2011.01) |

(52) U.S. Cl.
CPC *H04N 5/04* (2013.01); *A63B 24/00* (2013.01); *H04N 21/236* (2013.01); *H04N 21/242* (2013.01); *H04N 21/4223* (2013.01); *H04N 21/4307* (2013.01); *H04N 21/4524* (2013.01)

(58) Field of Classification Search
CPC ........... H04N 5/04; H04N 5/262; H04N 5/06; H04N 21/8547; H04N 21/242; G01S 3/02; G01S 5/0009; G01S 5/02; G01S 5/04; G01S 1/02
USPC .......... 348/500, 516, 510, 513, 512
IPC ................ H04N 5/04,5/262
See application file for complete search history.

(56) References Cited

U.S. PATENT DOCUMENTS

| | | | |
|---|---|---|---|
| 2005/0239601 A1* | 10/2005 | Thomas | 482/1 |
| 2010/0211966 A1* | 8/2010 | Zhang et al. | 725/10 |
| 2013/0201341 A1* | 8/2013 | Meadow et al. | 348/159 |

* cited by examiner

*Primary Examiner* — Sherrie Hsia
(74) *Attorney, Agent, or Firm* — Jonathan A. Kidney; TechLaw LLP

(57) ABSTRACT

The pending disclosure includes a computer server receiving a video file and a global positioning system (GPS) data file. The video file includes video frames each having a timestamp and the GPS data file includes portions of geographic data each having a timestamp. Further, the computer server receives video user input from a user device indicating a user selection of a synchronization video frame and a GPS user input from the user device indicating a user selection of a synchronization portion of geographic data. The computer server processes the selected synchronization video frame and the synchronization portion of geographic data to determine the timestamp of both the synchronization video frame and the synchronization portion of the geographic data. Further, the computer server synchronizes the GPS data file with the video file based on the timestamp of the synchronization video frame and the synchronization portion of the geographic data.

20 Claims, 10 Drawing Sheets

VIDEO AND MAP DATA SYNCHRONIZATION FOR SIMULATED ATHLETIC TRAINING

BACKGROUND OF THE INVENTION

The current state of the art for simulating outdoor athletic training in an indoor environment extends in a variety of directions. For example, current state of the art allows a user to download a software application onto a computer. The user may have a video file stored on the computer, the video file containing content directed to a bike ride over a bike trail. Further, the user may have a GPS data file stored on the computer that contains GPS information regarding the bike trail. The user may implement the software application to synchronize the video file with map views based on the GPS data file for future playback. The user may utilize the future playback during indoor bike training to simulate riding the outdoor bike trail.

However, the current state of the art has several limitations that include utilizing the software application on a user computer rather than on a cloud server. Further, the synchronization process is cumbersome as it requires the user to select several points in the video file and a corresponding point in map views based on the GPS data file to initiate video-map view/GPS data synchronization. In addition, such current state of the art requires the user to edit the video file and the GPS data file to be substantially the same length such that the software application can attempt to perform the synchronization process.

Other state of the art applications include providing video of a bike trail synchronized with map views based on GPS data to users on a local area network (e.g. CompuTrainer/RacerMate/VeloTrain). However, the limitations of such current state of art include the inability for users to upload their own recorded video content (e.g. crowdsourcing) and GPS/Performance data to a cloud server across the Internet and synchronize such data with each other.

Accordingly, there is a need for synchronizing uploaded video with map views based on GPS and performance data and presenting such synchronized video over the Internet to simulate outdoor athletic training.

BRIEF DESCRIPTION OF THE SEVERAL VIEWS OF THE DRAWINGS

The accompanying figures, where like reference numerals refer to identical or functionally similar elements throughout the separate views, together with the detailed description below, are incorporated in and form part of the specification, and serve to further illustrate embodiments of concepts that include the claimed invention, and explain various principles and advantages of those embodiments.

Figure 1:
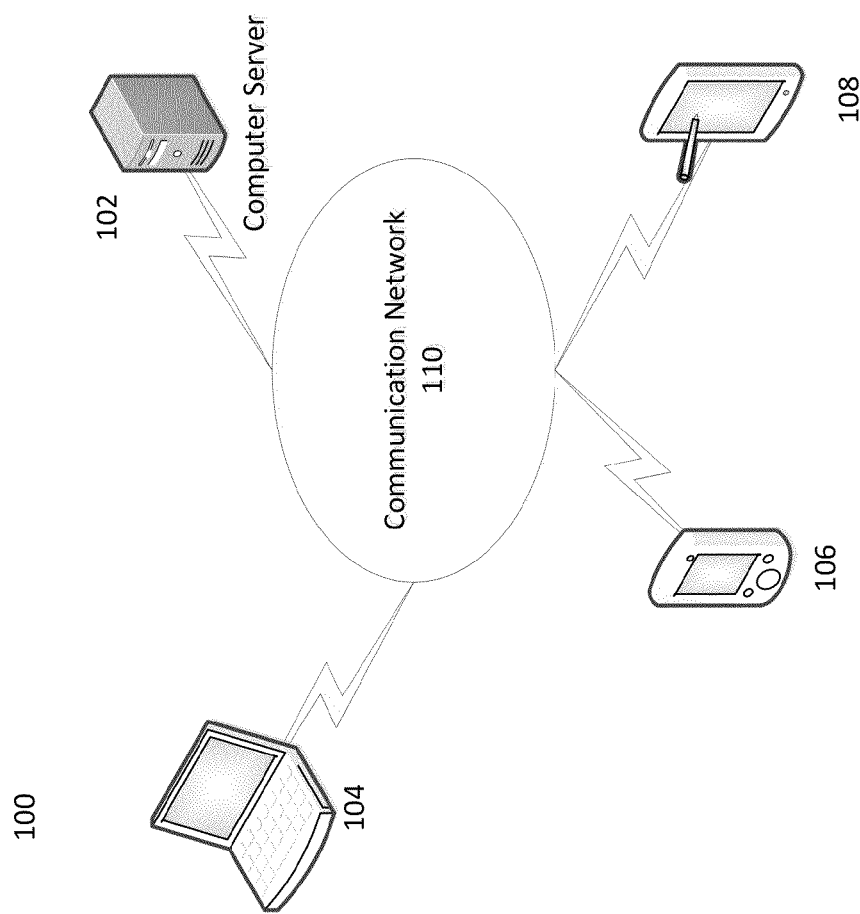
FIG. 1 is a block diagram of a system for synchronizing uploaded video with map views based on GPS and performance data and presenting such synchronized video over the Internet to simulate outdoor athletic training, in accordance with some embodiments.

Skilled artisans will appreciate that elements in the figures are illustrated for simplicity and clarity and have not necessarily been drawn to scale. For example, the dimensions of some of the elements in the figures may be exaggerated relative to other elements to help to improve understanding of embodiments of the present invention.

The apparatus and method components have been represented where appropriate by conventional symbols in the drawings, showing only those specific details that are pertinent to understanding the embodiments of the present invention so as not to obscure the disclosure with details that will be readily apparent to those of ordinary skill in the art having the benefit of the description herein.

DETAILED DESCRIPTION OF THE INVENTION

The illustrative embodiments described in the detailed description, drawings, and claims are not meant to be limiting. Other embodiments may be utilized, and other changes may be made, without departing from the scope of the subject matter presented herein. It will be readily understood that the aspects of the present disclosure, as generally described herein, and illustrated in the Figures, can be arranged, substituted, combined, separated, and designed in a wide variety of difference configurations, all of which are explicitly contemplated herein. Further, in the foregoing description, numerous details are set forth to further describe and explain one or more embodiments. These details include system configurations, block module diagrams, flowcharts (including transaction diagrams), and accompanying written description. While these details are helpful to explain one or more embodiments of the disclosure, those skilled in the art will understand that these specific details are not required in order to practice the embodiments.

As will be appreciated by one skilled in the art, aspects of the present disclosure may be embodied as an apparatus that incorporates some software components. Accordingly, some embodiments of the present disclosure, or portions thereof, may combine one or more hardware components such as microprocessors, microcontrollers, or digital sequential logic, etc., such as processor with one or more software components (e.g., program code, firmware, resident software, micro-code, etc.) stored in a tangible computer-readable memory device such as a tangible computer memory device, that in combination form a specifically configured apparatus that performs the functions as described herein. These combinations that form specially-programmed devices may be generally referred to herein "modules". The software component portions of the modules may be written in any computer language and may be a portion of a monolithic code base, or may be developed in more discrete code portions such as is typical in object-oriented computer languages. In addition, the modules may be distributed across a plurality of computer platforms, servers, terminals, mobile devices and the like. A given module may even be implemented such that the described functions are performed by separate processors and/or computing hardware platforms.

Embodiments of the present disclosure describe methods, systems and devices to synchronize uploaded video with map views based on GPS and performance data and presenting such synchronized video and map views over the Internet to simulate outdoor athletic training. Such methods, systems, and devices include a computer server receiving over a communication network a video file and a global positioning system (GPS) data file. The video file may include one or more video frames each video frame having a video timestamp and the GPS data file may include one or more portions of geographic data such that each portion of geographic data may have a timestamp. Further, the computer server may receive, over the communication network, video user input from a user device indicating a user selection of a synchronization video frame that is one of the video frames of the video file. In addition, the computer server may receive over the communication network GPS user input from the user device indicating a user selection of a synchronization portion of geographic data. In one embodiment, such a selected synchronization portion of geographic data may be part of the GPS data file. In another embodiment, such a selected synchronization portion of geographic data may not be part of the GPS data file. The computer server may process the selected synchronization portion of geographic data to determine a nearest portion of the geographic data that is part of the GPS data and designate such nearest portion of the geographic data as corresponding to the synchronization video frame. Moreover, the computer server may process the selected synchronization video frame and the portion of geographic data corresponding to the synchronization video frame to determine the timestamp of the synchronization video frame and the timestamp of the portion of the geographic data. Further, the computer server synchronizes the GPS data file with the video file based on the timestamp of the synchronization video frame and the timestamp of the portion of the geographic data corresponding to the synchronization video frame.

FIG. 1 is a block diagram of a system 100 for synchronizing uploaded video with map views based on GPS and performance data and presenting such synchronized video with map views over a communication network 110 to simulate outdoor athletic training, in accordance with some embodiments. The system 100 includes one or more computing devices (104, 106, 108) coupled to the computer server 102 over a communication network. The computing devices (104, 106, 108) may include laptop computers, desktop computers, tablet computers, smartphones, video camera, global positioning system (GPS) device, and mobiles devices. The communication network 110 may be the Internet, a wide area network, a local area network, a cellular network, a wireless network, or any combination thereof. In one embodiment, the computer server 110 may host a crowdsourcing service on a website that allows a user to upload a video file from a computing device and GPS data such that video synchronized to map views based on the GPS data to be streamed, downloaded, or otherwise presented to one or more users. Users that are presented with the synchronized video may be called viewers. Further, such viewers may stream, download, or otherwise view the synchronized video on a tablet computer or other user computing device while riding an indoor exercise bike to simulate outdoor training using the bike ride shown in the synchronized video.

In other embodiments, the computer server 100 may host a wireless application that allows a user to crowdsource, that is, to upload video and GPS data from one or more mobile computing devices (e.g. portable video camera and GPS devices) to be streamed, downloaded, or otherwise presented to and viewed by one or more viewers. In a further embodiment, the user may upload a video file and a GPS data file from a user computing device 104 to the computer server 102. The video file may have been transferred from a video camera device and stored on the user computing device 104 or portable memory device. In some embodiments, the video was recorded and is shown at a rate of 32 frames per second. Also, the GPS data may have been transferred from a GPS device and stored on the user computing device 104 or portable memory device. In some embodiments, the GPS data includes longitude, latitude, and elevation geographic data/information. In other embodiments, the GPS data may be used to calculate a moving average speed of the biker on the bike ride recorded in the video to assist in synchronizing the video with the GPS data file. Further, the GPS data file may not include data for a significant amount of time due to various reasons. These reasons include that there may not have been a clear line of sight to a GPS satellite orbiting overhead, GPS information could not be received because of interference of the ambient environment, and/or GPS information is not recorded because the GPS device or the overhead GPS system has a malfunction.

The user uploads the video file and the GPS data file using a user interface on the user computing device 104. Further, the computer server 102 receives over the communication network 110 the video file and the GPS data file from the user computing device 104. The video file includes one or more video frames each video frame having a video timestamp. Further, the GPS data file includes one or more portions of geographic data each portion of geographic data having a timestamp. The computer server 102 provides a user interface to the user on user computing device 104. The user inputs and the computer server 102 receives over the communication network 110 from the user computing device 104 video user input indicating a user selection of a synchronization video frame that is one of the one or more video frames of the video file. In addition, the computer server 102 receives over the communication network 110, GPS user input from the user computing device indicating a user selection of a synchronization portion of geographic data. Moreover, the synchronization portion of the geographic data may be one of the one or more portions of the geographic data in the GPS data file. The user interface may present the geographic data in a map view. In some embodiments, the map view may render a map image based one the geographic data in the GPS data file. In alternate embodiments, the map view may render a satellite image based on the geographic data in the GPS data file. In further embodiments, the user interface allows a user to select a synchronization map view corresponding to the synchronization portion of the geographic data. The user interface may then determine and transmit the synchronization portion of the geographic data to the computer server 102.

The user may be directed by the user interface to select a synchronization video frame and a synchronization map view each showing a synchronization landmark. For example, a synchronization video frame may show an intersection of Maple Street and Elm Street. Further, the synchronization map view may also show the intersection of Maple Street and Elm Street (e.g. as a map image, satellite image, etc.). Thus, in both the synchronization video frame and the synchronization map view, the synchronization landmark is the intersection of Elm Street and Maple Street.

In addition, the computer server 102 processes the selected synchronization video frame and the synchronization portion of geographic data (corresponding to the synchronization map view) to determine the timestamp of the synchronization video frame and the timestamp of the synchronization portion of the geographic data (i.e. portion of geographic data corresponding to the synchronization video frame). Further, the computer server 102 synchronizes the GPS data file with the video file based on the timestamp of the synchronization video frame and the timestamp of the synchronization portion of the geographic data as described herein. That is, in one embodiment, the computer server 102 analyzes the timestamp for each portion of geographic data and selects a synchronization portion of geographic data (i.e. portion of geographic data corresponding to the synchronization video frame) that has a timestamp closest to the timestamp of the synchronization video frame. The computer server 102 then synchronizes the video file and the geographic data based on the timestamp of the synchronization video frame and the timestamp of the synchronization portion of the geographic data.

Moreover, the video file is an unedited video file recorded and stored by a video camera in video camera memory that has been transferred to user computing device 104 (or a portable memory device) to be uploaded. The GPS data file is an unedited GPS data file recorded and stored by a GPS device that has been transferred to user computing device 104 (or a portable memory device) to be uploaded. In one embodiment, because uploading of a video file may take some time, the computer server 102 generates a notification to the user after the video file and GPS data file are received. The notification may be an email message, a text message, an alert (mobile), etc.

In alternate embodiments, the computer server 102 may modify a length of the GPS data file based on synchronizing the GPS data file with the video file. For example, the video file may contain two hours of video. However, upon analyzing the GPS data, the computer server 102 may determine there are four hours of GPS data, one hour before the video is captured and one hour after the video has been captured. Thus, the computer server 102 may edit the length of the GPS data file by pruning (deleting) the first hour of the GPS data file and the last hour of the GPS data file to match data to correct video frame.

In some embodiments, the GPS data include performance data (e.g. heart rate). Thus, the computer server 102 may synchronize performance data with the video file. The performance data may have one or more portions of performance data with each portion of performance data having a timestamp. The computer server 102 synchronizes the video file with performance data based on the timestamp of the synchronization video frame and the corresponding timestamp of the portion of performance data.

The computer server 102 displays the uploaded video file synchronized with map views based on the uploaded GPS data. In additional embodiments, the computer server 102 provides the synchronized video file with map views based on the GPS data file to one or more viewer computing device (106, 108) over the communication network 110. The computer server 102 may stream, download, or otherwise present the synchronized video file with the map views to the viewer computing devices. A viewer may be a biker that is using the presented synchronized video file to simulate an outdoor environment for training and recreational purposes.

Although some of the embodiments described in the present disclosure are directed to a biker using the presented synchronized video file to simulate an outdoor environment for training and recreational purposes, alternative embodiments may include uploading video and GPS/Performance data associated with skiing, snowboarding, snowmobiling, off-terrain vehicle riding, running, hiking and walking trails or any other outdoor activity recorded with video and GPS/Performance data that can be synchronized and presented to viewers to simulate an outdoor environment for training and recreational purposes.

Figure 2:
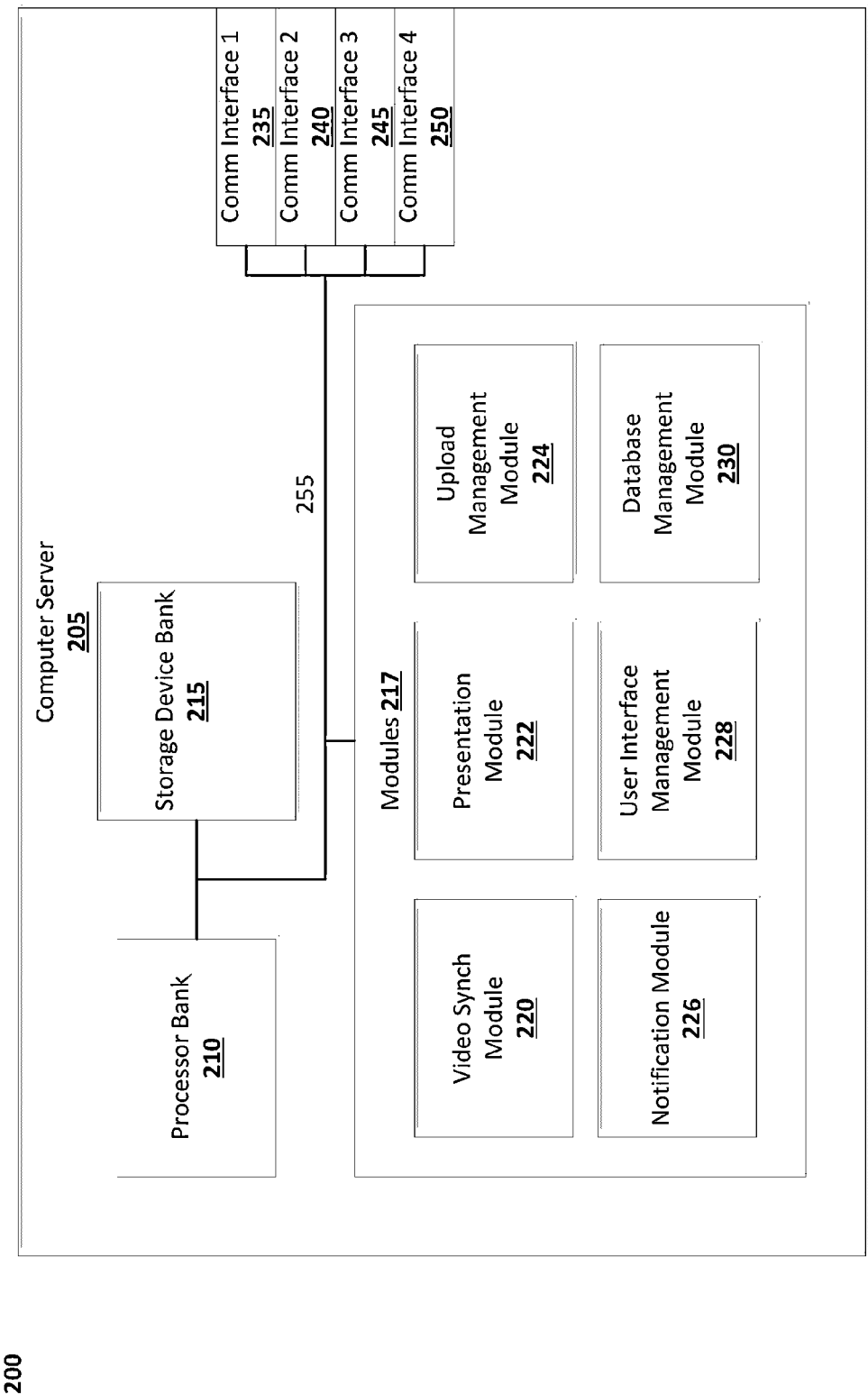
FIG. 2 is a block diagram of a computing device used in synchronizing uploaded video with map views based on GPS and performance data and presenting such synchronized video over the Internet to simulate outdoor athletic training in accordance with some embodiments.

FIG. 2 is a block diagram of a computing device 205 used in synchronizing uploaded video with map views based on GPS and performance data and presenting such synchronized video over the Internet to simulate outdoor athletic training in accordance with some embodiments. Such a computing device 205 may be a computer server that may be used in a system shown in FIG. 1. The computer server 205 may include several different components such as a processor bank 210, storage device bank 215, one or more software applications, that when executed by a processor from specifically-configured modules (as described herein) 217, and one or more communication interfaces (235-250). In some embodiments the components of computer server 205 may not be located within one computer server 205 but distributed among a plurality of computer servers and/or computing devices.

The processor bank 210 may include one or more processors that may be co-located with each other or may be located in different parts of the computer server 205. The storage device bank 215 may include one or more storage devices. Types of storage devices may include memory devices, electronic memory, optical memory, and removable storage media. The one or more modules 217 may include a video synchronization module 220, a presentation module 222, an upload management module 224, a notification module 226, a user interface management module 228, and a database management module 230. The modules 217 may be implemented by the one or more processors in the processor bank 210.

The computer server 205 receives, over a communication network, a video file and a global positioning system (GPS) data file uploaded from a user computing device. The upload management module 224 receives and processes the video file and the GPS data file. The video file includes one or more video frames each video frame having a video timestamp. Further, the GPS data file includes one or more portions of geographic data each portion of geographic data having a timestamp. When the upload is complete, in one embodiment, the upload management module 224 communicates with the notification module to send a message to the user that the uploading of the video file and the GPS data file. This message may be transmitted via email or a text message as well as a pop-up message on a user interface or as an alert notification (used in mobile devices).

In one embodiment, the presentation module 222 streams, downloads, or otherwise presents the video file and map views based on the uploaded GPS data to a user interface on a user computing device in conjunction with the user interface management module 228. Further, the computer server 205 receives, over the communication network, video user input from the user computing device indicating a user selection of a synchronization video frame that is a frame from the video file. In addition, the computer server 205 receives, over the communication network, GPS user input from the user computer device indicating a user selection of a synchronization map view corresponding to a synchronization portion of geographic data that a portion of the geographic data. The synchronization video frame displays a synchronization landmark and the synchronization map view based on synchronization portion of geographic data that includes geographic information also displays the synchronization landmark. Thus, the user selects the synchronization video frame and the synchronization map view because the user recognizes the synchronization landmark in both the synchronization video frame and the synchronization map view.

The video user input and the GPS user input is received from the user interface management module 228 and provided to the video synchronization module 220. In one embodiment, the video synchronization module 220 processes the selected synchronization video frame and the synchronization map view to determine the corresponding synchronization portion of geographic data. Such a portion of geographic data may be considered to further correspond to the synchronization video frame. Further, the video synchronization module determines the timestamp of the synchronization video frame and the timestamp of the synchronization portion of the geographic data. Further, the video synchronization module 220 synchronizes the GPS data file with the video file based on the timestamp of the synchronization video frame and the timestamp of the synchronization portion of the geographic data based on the techniques described herein. That is, in one embodiment, the video synchronization module 220 analyzes the timestamp for each portion of geographic data and selects a synchronization portion of geographic data that has a timestamp closest to the timestamp of the synchronization video frame. The video synchronization module 220 then synchronizes the video file and the geographic data based on the timestamp of the synchronization video frame and the timestamp of the synchronization portion of the geographic data.

In addition, the video synchronization module 220 modifies a length of the GPS data file based on synchronizing the GPS data file with the video file. That is, in some embodiments, the GPS data file may be longer than the video file. For example, the GPS data file recorded data one hour prior to the video file until one hour after the video file. The video synchronization module 220 edits the GPS data file by modifying the length of the GPS data file to coincide with the duration of the video file based on timestamps of data recorded in the GPS data file and timestamps of video frames from the video file. Such a capability allows the computer server 205 to receive an unedited video file recorded and stored by a video camera in video camera memory (then transferred to a user computing device or portable memory device for upload) and an unedited GPS data file recorded and stored by a GPS device (then transferred to a user computing device or portable memory device for upload).

In further embodiments, the GPS data include performance data comprising one or more portions of performance data, each portion having a timestamp. The video synchronization module 220 may also synchronize performance data with the video file based on the timestamp of the synchronization video frame. That is, the video synchronization module analyzes the timestamp for each portion of performance data and selects a synchronization portion of performance data that has a time stamp closest to the time stamp of the synchronization vide frame. The video synchronization module 220 then synchronizes the video file and the performance data based on the time stamp of the synchronization video frame and the timestamp of the synchronization portion of the performance data.

In additional embodiments, the presentation module 222 may stream, download or otherwise present the synchronized video file synchronized with map views generated based on the synchronized GPS data to one or more viewing computing devices over the communication network. The viewing computing devices may be a device operated by the user that uploaded the video file and GPS data file or may be other users that would like to view the synchronized video file with GPS data for simulated outdoor athletic training that allows for automatic presentation and use.

Each of the communication interfaces (235-250) may be software or hardware associated in communicating to other devices. The communication interfaces (235-250) may be of different types that include a user interface, USB, Ethernet, WiFi, WiMax, wireless, optical, cellular, or any other communication interface coupled to a communication network. One or more of the communication interfaces (235-250) may be coupled to a user interface known in the art.

An intra-device communication link 255 between the processor bank 310, storage device bank 215, modules 217, and communication interfaces (230-245) may be one of several types that include a bus or other communication mechanism.

Figure 3:
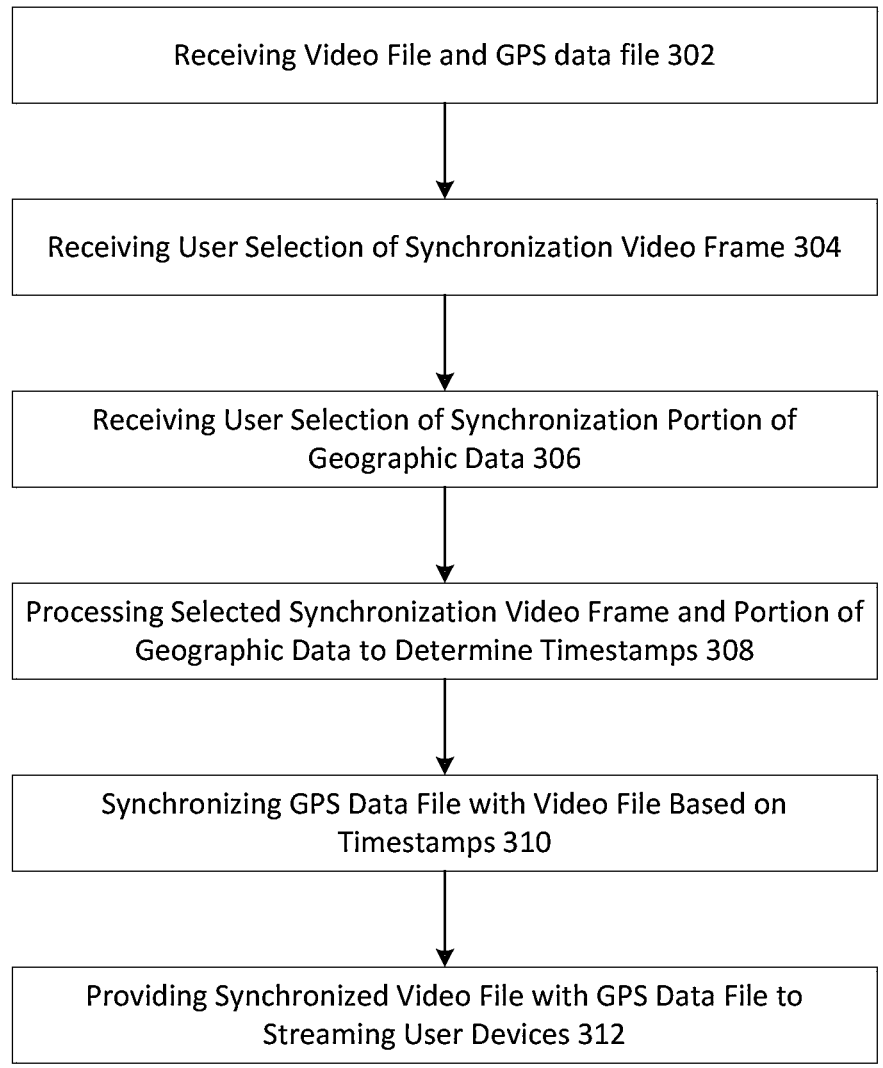
FIGS. 3-4 are flowcharts of methods of synchronizing uploaded video with map views based on GPS and performance data and presenting such synchronized video over the Internet to simulate outdoor athletic training in accordance with some embodiments.

FIG. 3 is flowchart of a method 300 for synchronizing uploaded video with map views based on GPS and performance data and presenting such synchronized video over the Internet to simulate outdoor athletic training in accordance with some embodiments. The method 300 includes a computer server receiving, over a communication network, a video file and a global positioning system (GPS) data file, as shown in block 302. The video file including one or more video frames each video frame having a video timestamp. The GPS data file including one or more portions of geographic data each portion of geographic data having a timestamp. The method 300 further includes the computer server receiving, over the communication network, video user input from a user device indicating a user selection of a synchronization video frame that is one of the one or more video frames of the video file, as shown in block 304. In addition, method 300 includes the computer server receiving, over the communication network, GPS user input from the user device indicating a user selection of a synchronization map view corresponding to a synchronization portion of geographic data that is one of the one or more portions of the geographic data, as shown in block 306. The synchronization video frame and the synchronization map view, each display a synchronization landmark and the synchronization portion of geographic data includes geographic information relating to the synchronization landmark. Thus, the user selects the synchronization video frame and synchronization map view because the synchronization landmark is found in both. Thus, the selected synchronization portion of geographic data can be said to correspond to the synchronization video frame.

Moreover, the method 300 includes the computer server processing the selected synchronization video frame as well as the synchronization map view and corresponding synchronization portion of geographic data to determine the timestamp of the synchronization video frame and the timestamp of the synchronization portion of the geographic data, as shown in block 308. As part of the synchronization, the computer server may modify a length of the GPS data file based on synchronizing the GPS data file with the video file. That is, if the GPS data is longer than the video file, the computer server modifies the length of the GPS file to coincide in time with the duration of video file. Thus, the video file can be an unedited video file recorded and stored by a video camera in video camera memory (and transferred to a user computing device or portable memory device to be uploaded and the GPS data file is an unedited GPS data file recorded and stored by a GPS device (and transferred to a user computing device or portable memory device to be uploaded).

The method 300 further includes the computer server synchronizing the GPS data file with the video file based on the timestamp of the synchronization video frame and the timestamp of the synchronization portion of the geographic data (i.e. portion of geographic data corresponding to synchronization video frame), as shown in block 310. That is, in one embodiment, the computer server analyzes the timestamp for each portion of geographic data and selects a synchronization portion of geographic data that has a timestamp closest to the timestamp of the synchronization vide frame. The computer server then synchronizes the video file and the geographic data based on the timestamp of the synchronization video frame and the timestamp of the synchronization portion of the geographic data.

In addition, the method 300 includes the computer server providing the synchronized video file with map views based on the GPS data file to one or more viewing user computing devices over the communication network, as shown in block 312. The viewing user devices may be operated by the user that uploaded the video file and GPS data file or may be other users that would like to view the synchronized video file with the GPS data file to simulate outdoor athletic training.

Figure 4:
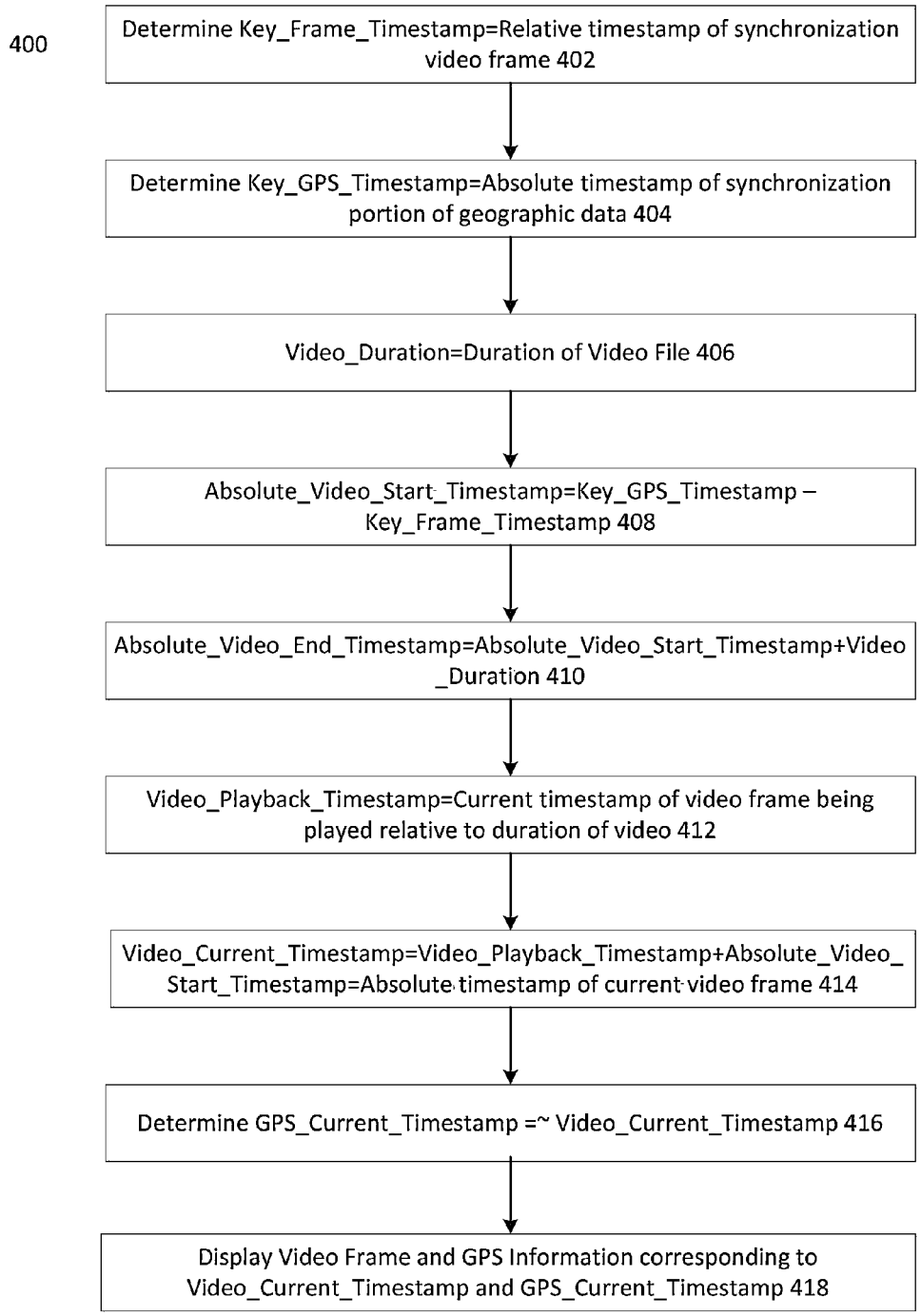

FIG. 4 is a flowchart of a method 400 for synchronizing uploaded video with map views based on GPS and performance data and presenting such synchronized video over the Internet to simulate outdoor athletic training in accordance with some embodiments. As described herein the pending disclosure a user selects a synchronization landmark in both a synchronization video frame and a synchronization map view corresponding to a synchronization portion of the geographic data (GPS data) (i.e. portion of geographic data corresponding to synchronization video frame). The method 400 includes a computer server processing the synchronization video frame to determine a Key_Frame_Timestamp parameter which is the relative timestamp of the synchronization video frame from the beginning of the video file, as shown in block 402. For example, the user may select a bridge landmark two minutes and 33 seconds (2:33) after the start of the video file. Hence, the Key_Frame_Timestamp parameter has a value of 2:33. The method 400 further includes processing the synchronization portion of the geographic data to determine a Key_GPS_Timestamp parameter which is the absolute timestamp of the synchronization portion of the geographic data (GPS data file), as shown in block 404. For example, the user may select the synchronization map view showing the same bridge landmark. The computer server determines the corresponding synchronization portion of the geographic data to the synchronization map view and finds that the associated timestamp of the synchronization portion is 08:15:47 (fifteen minutes and forty-seven seconds after 8 o'clock in the morning). Hence, the Key_GPS_Timestamp parameter has a value of 08:15:47. In addition, the computer server processes the video file to determine a Video_Duration parameter as the duration of the video file, as shown in block 406. For example, the video file may be two hours, 17 minutes and 29 seconds long.

Moreover, the method 400 includes the computer server calculating an Absolute_Video_Start_Timestamp parameter value as equal to the difference in value of the Key_GPS_Timestamp parameter with the value of the Key_Frame_Timestamp parameter, as shown in block 408. That is, the Absolute_Video_Start_Timestamp is the absolute timestamp of the first video frame of the video file. For example, if the Key_GPS_Timestamp value is 08:15:47 and the Key_Frame_Timestamp value is 2:33 then the Absolute_Video_Start_Timestamp value is 08:13:14 (i.e. thirteen minutes and fourteen seconds after 8 o'clock in the morning). The method 400 further includes calculating Absolute_Video_End_Timestamp parameter value to be the sum of the value of the Absolute_Video_Start_Timestamp parameter and the value of the Video_Duration parameter, as shown in block 410. That is, the absolute timestamp of the end video frame is calculated based on the absolute timestamp of the first video frame in addition to the duration of the video file. For example, the value of the Absolute_Video_Start_Timestamp parameter is 08:13:14 and the Video Duration parameter may have a value of 02:17:29 (two hours, 17 minutes and 29 seconds) such that the Absolute_Video_End_Timestamp parameter has a value of 10:30:43 (i.e. thirty minutes and twenty-nine seconds after 10 o'clock).

The method 400 may then provide playback (e.g. streaming, downloading, etc.) to one or more users of the synchronized video with map views based on the GPS data file. The method 400 includes the computer server determining a Video_Playback_Timestamp parameter that is equal to the current timestamp of a video frame being played relative to a duration of the video file, as shown in block 412. For example, the Video_Playback_Timestamp value may be 3:13 (three minutes, and 13 seconds from the start of the video file). In addition, the method 400 includes a computer server calculating a value of a Video_Current_Timestamp parameter that is the sum of the value of the Video_Playback_Timestamp parameter with the value of the Absolute_Video_Start_Timestamp parameter which is equal to the value of the absolute timestamp of the current video frame, as shown in block 414. For example, the value of Video_Playback_Timestamp may be 3:13 and the value of Absolute_Video_Start_Timestamp may be 8:13:14 such that the value of Video_Current_Timestamp is 8:16:27. Also, the method 400 includes the computer server determining a GPS_Current_Timestamp parameter value nearest/closest to the Video_Current_Timestamp, as shown in block 416. For example, the closest portion of geographic data to the Video_Current_Timestamp may be 8:16:31 and hence is the value of GPS_Current_Timestamp. Moreover, the method 400 includes displaying video frame and a map view based on GPS information corresponding to the Video_Current_Timestamp parameter and GPS_Current_Timestamp parameter, respectively, as shown in block 418.

Figure 5:
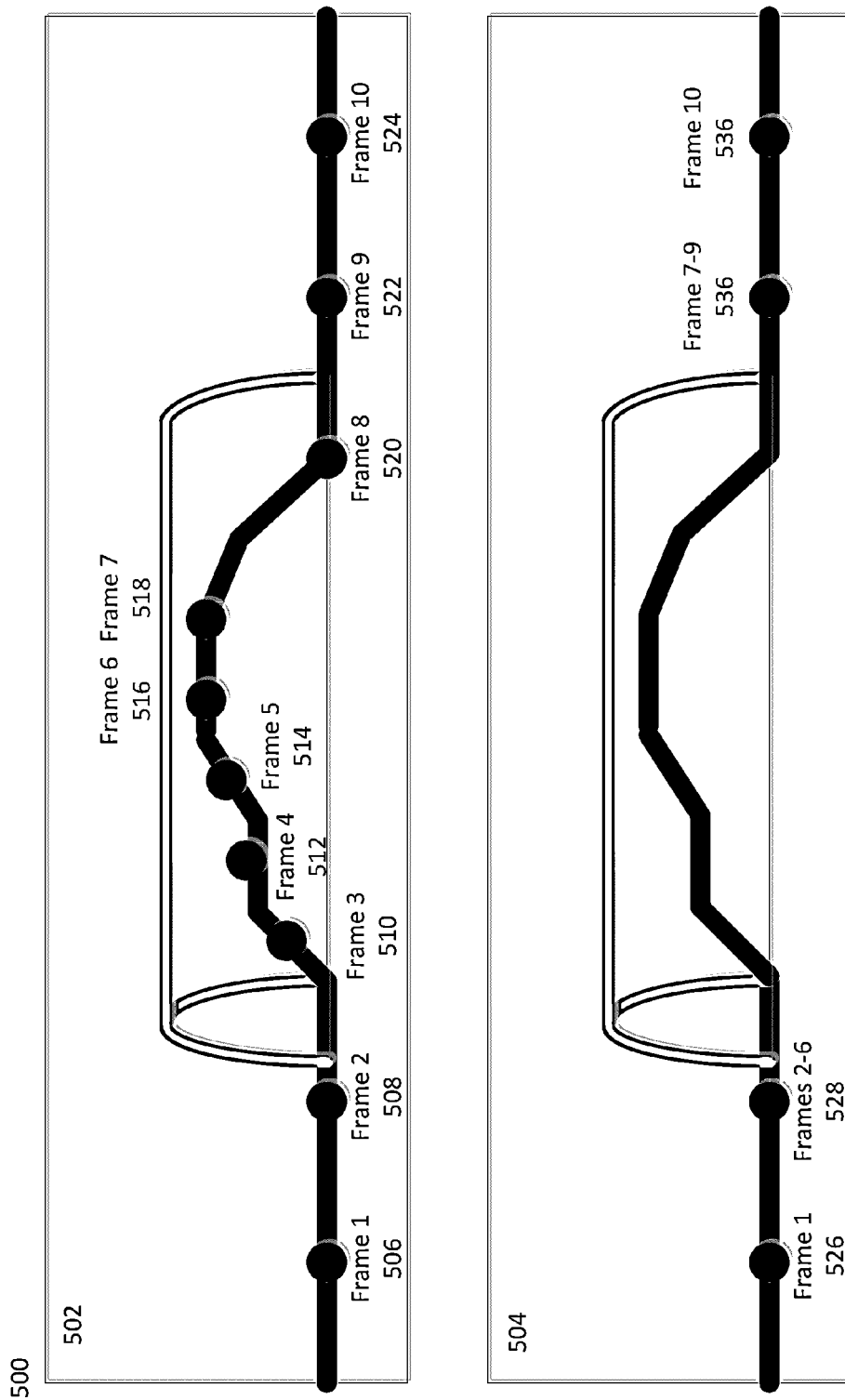
FIGS. 5-7 are frame-by-frame diagrams of a video synchronized with map views based on GPS and performance data in accordance with some embodiments.
Figure 6:
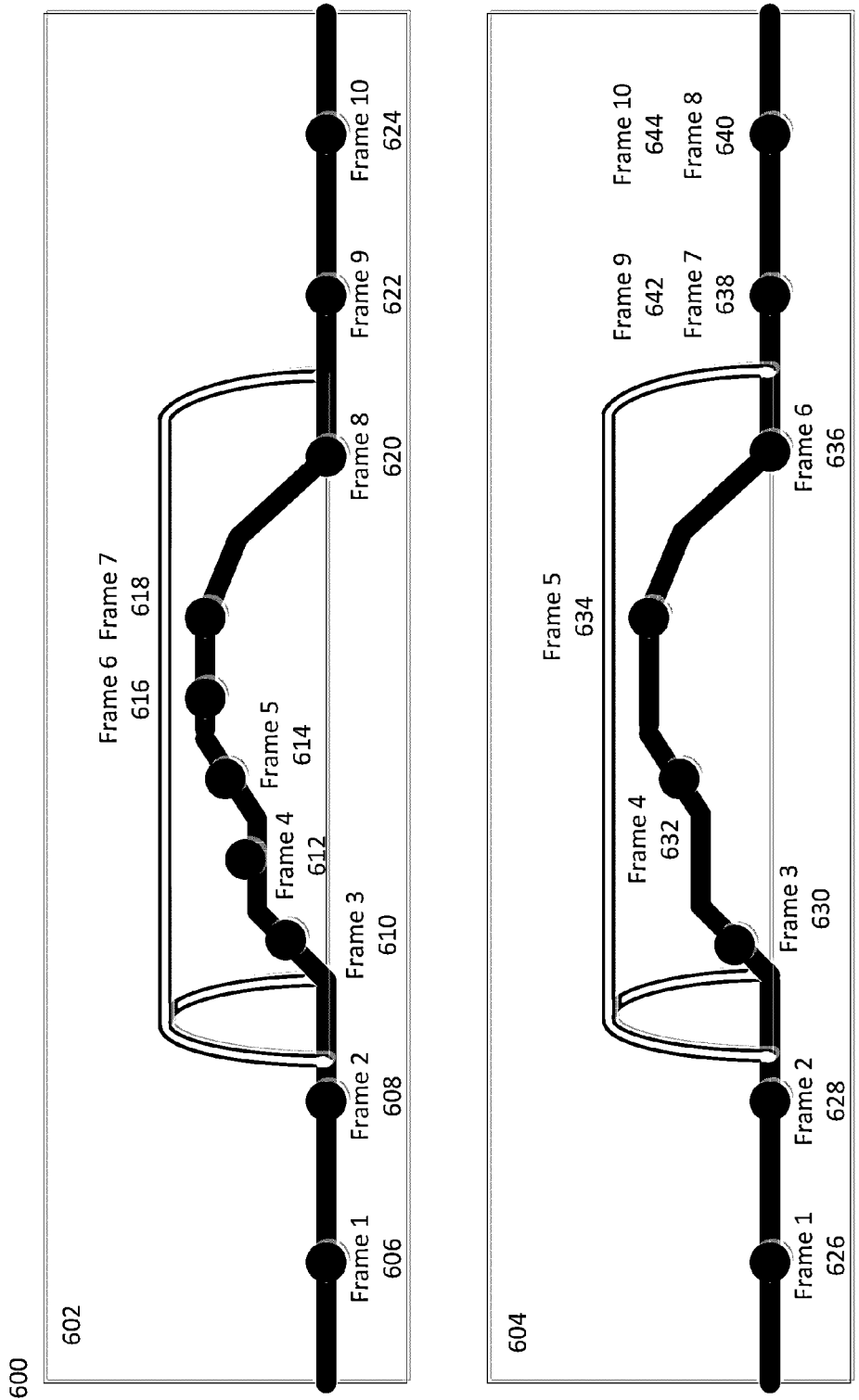
Figure 7:
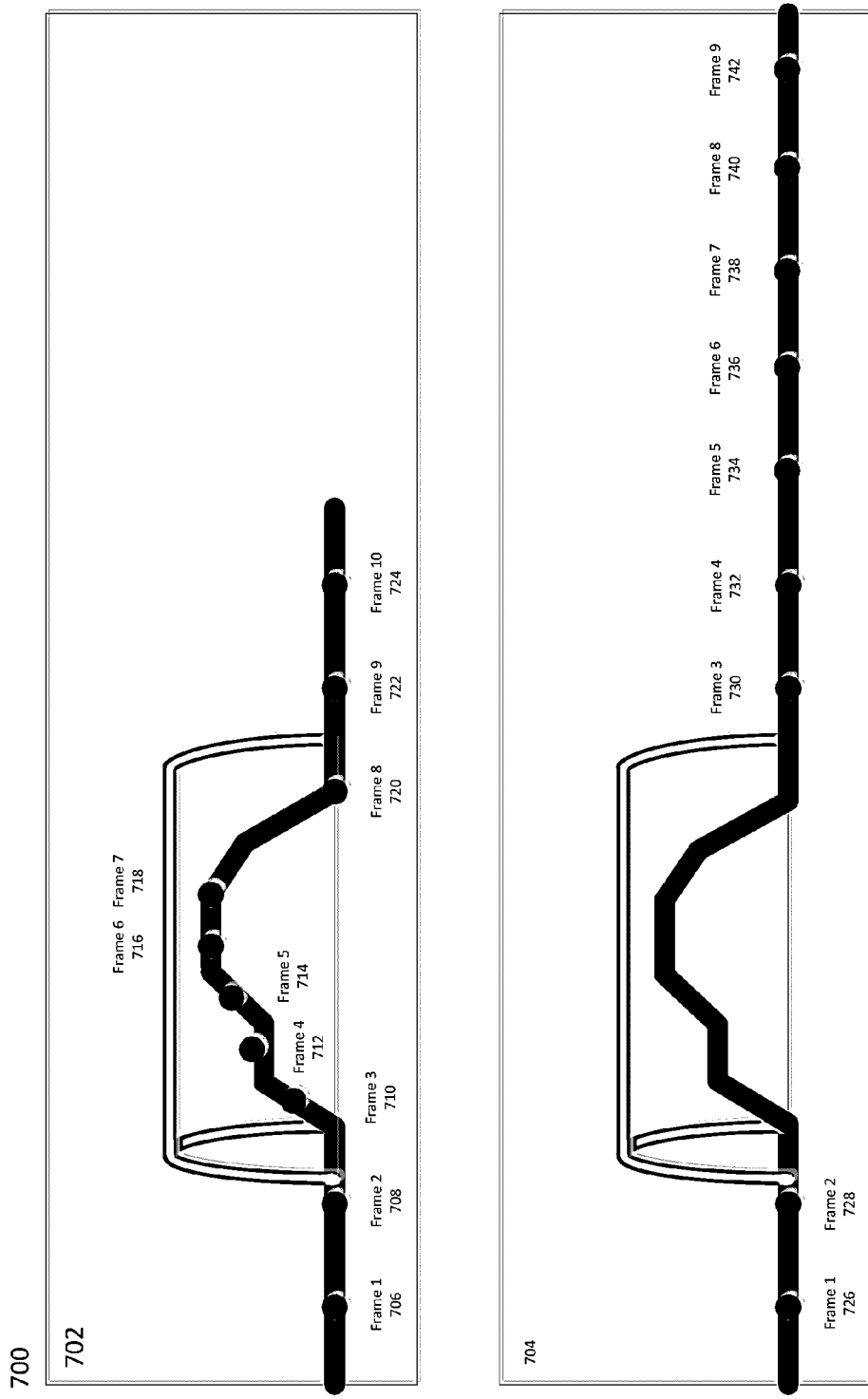

FIGS. 5-7 are frame-by-frame diagrams of a video synchronized with map views based on GPS and performance data in accordance with some embodiments. FIGS. 6-7 show the ways in which the systems, methods and devices in the present disclose synchronize uploaded video with uploaded GPS/performance data and then present such synchronized video on a viewer device. Alternatively, FIG. 7 is a frame-by-frame diagram showing video and GPS/Performance data are not synchronized based on the techniques described herein but are synchronized using prior art techniques.

FIG. 5 is a frame-by-frame diagram of a video 502 synchronized with map views 504 based on GPS and performance data in accordance with some embodiments. The video 502 and map view 504 may be streamed to a user computing device. The video 502 may be uploaded video by the user (or another user) to a computer server. The map views 504 are generated based on GPS and performance data uploaded by the user. Such video 502 and GPS and performance data, hence the map views 504, are synchronized based on the techniques described herein.

In one embodiment, video 502 and map views 504 show a biker riding on a road and through a tunnel. Further, the road as several inclines and declines within the tunnel. A frame 1 506 of the video 502 shows a biker at point some distance from the entrance of the tunnel. Further, based on the techniques described herein, a frame 1 526 of the map view 504 shows a geographic location of the biker also some distance from the entrance of the tunnel. In addition, the video 502 shows frame 2 508 when the biker is at the entrance of the tunnel and map view 504 shows frame 2 528 which is the corresponding geographic location at the entrance of the tunnel. Video 502 continues to show frames 3-6 as the video shows a biker moving through the tunnel. However, there may be no corresponding GPS data for geographic locations within the tunnel. This may be due to the GPS device recording the GPS data has no communication with the GPS satellite system orbiting overhead due to interference from being within the tunnel. Thus, based on the techniques described herein, the map view 504 continues to show the geographic location corresponding to the entrance of the tunnel. That is, as described in the techniques herein, the map view 504 corresponding to the GPS data with timestamp closest to the timestamp of the current video frame. Thus, for frames 3-6 (510-516) in video 502, the closest timestamped GPS data corresponds to the entrance of the tunnel 528 as shown in the map view 504. However, for frames 7-8 (518-520) of the video 502, the closest timestamped GPS data corresponds to a geographic location closest to the tunnel exit 536. Further, when video 502 shows frame 9 522 at the exit of the tunnel, based on the techniques described herein, the map view 504 shows the exit of the tunnel as the geographic location. In addition, when the video 502 shows frame 10 524 where the biker is some distance from the exit of the tunnel, the map view 504 shows frame 10 536 also some distance from the exit of the tunnel.

Note, in some embodiments, video is recorded and shown at 32 frames per second. However, the frame-by-frame diagrams in FIGS. 5-7 and do not necessarily show consecutive frames.

FIG. 6 is a frame-by-frame diagram of a video 602 synchronized with map views 604 based on GPS and performance data in accordance with some embodiments. The video 602 and map view 604 may be streamed to a user computing device. The video 602 may be uploaded video by the user (or another user) to a computer server. The map view 604 is generated based on GPS and performance data uploaded by the user. Such video 602 and GPS and performance data, hence the map views 604, are synchronized based on the techniques described herein.

In one embodiment, video 602 and map views 604 show a biker riding on a road and through a tunnel. Further, the road as several inclines and declines within the tunnel. A frame 1 606 of the video 602 shows a biker at point some distance from the entrance of the tunnel. Further, based on the techniques described herein, a frame 1 626 of the map view 604 shows a geographic location of the biker also some distance from the entrance of the tunnel. In addition, the video 602 shows frame 2 608 when the biker is at the entrance of the tunnel and map view 604 shows frame 2 628 which is the corresponding geographic location at the entrance of the tunnel. Video 602 continues to show frames 3-6 as the video shows a biker moving through the tunnel. However, there may be no corresponding GPS data for geographic locations within the tunnel. This may be due to the GPS device recording the GPS data has no communication with the GPS satellite system orbiting overhead due to interference from being within the tunnel. Thus, the computer server implementing the techniques described herein and providing the streaming video, may determine a moving average speed of the biker based on previous GPS data. For example, the computer server may analyze the GPS data corresponding to the frames of the map view 604. The distance between the location shown in frame 1 626 and frame 2 628 may be determined to be 0.1 miles. Further, the difference in timestamps between frame 1 626 and frame 2 628 may be 360 seconds (6 minutes).

Hence, the computer server may calculate the average speed of the biker at the entrance of the tunnel (608, 628) to be 6 miles per hour. In addition, there may be no GPS data corresponding to any geographic location within the tunnel. Thus, the computer server may generate extrapolated GPS data corresponding to the geographic locations within the tunnel. For example, frame 3 630 may correspond to 0.1 miles from the location of frame 2 628. Further, frame 4 632 may be another 0.1 miles from the location of frame 3 630. A similar calculation may be done to extrapolate GPS data for frames 5-6 (634-636).

In contrast, the video 602 shows the biker location based on the uploaded video file. Frame 3 610 of the video 602 may not be near the location of frame 3 630 of the map view 604 because the incline within the tunnel slows the biker speed. Hence, frame 3 610 may be at a location 0.08 miles from the location of frame 2 608. Frame 4 612 of the video 602 may not be near the location of frame 4 632 of the map view 604 because the incline within the tunnel further slows the biker speed. Hence, frame 4 610 may be at a location 0.07 miles from the location of frame 3 610. Moreover, video 602 shows the actual location of frames 5-8 (614-620).

Due to the change in speed by the biker within the tunnel, the frames 3-8 of the map view 604 that corresponds to frames 3-8 of the video 602 where the biker is located within the tunnel, may be out of synchronization. Consequently, locations of frame 7 618 and frame 8 620 of the video 602 may be shown to be within the tunnel but frame 7 638 and frame 8 640 are shown on the map view 604 to be outside the tunnel. However, when the frame 9 622 of the video file is presented and shows that the biker has exited the tunnel, using the techniques described herein, the computer server presents frame 9 642 showing that the geographic location is at the exit of the tunnel. Thus, the video 602 and the map view 604 based on the GPS data are resynchronized automatically based on the techniques described herein. Further, when the frame 10 624 of the video file is presented and shows that the biker is some distance from the exit of the tunnel, using the techniques described herein, the computer server presents frame 10 644 showing that the geographic location is also at some distance from the exit of the tunnel.

FIG. 7 is a frame-by-frame diagram of a video 702 synchronized with map views 704 based on GPS and performance data in accordance with some embodiments. The video 702 and map view 704 may be streamed to a user computing device. The video 702 may be uploaded video by the user (or another user) to a computer server. The map view 704 is generated based on GPS and performance data uploaded by the user. However, such video 702 and GPS and performance data, hence the map view 704, are not synchronized based on the techniques described herein but are synchronized using prior art techniques.

Video 702 and 704 show a biker riding on a road and through a tunnel. Further, the road as several inclines and declines within the tunnel. A frame 1 706 of the video 702 shows a biker at point some distance from the entrance of the tunnel. Further, based on prior art techniques, a frame 1 726 of the map view 704 shows a geographic location of the biker also some distance from the entrance of the tunnel. In addition, the video 702 shows frame 2 708 when the biker is at the entrance of the tunnel and map view 704 shows frame 2 728 which is the corresponding geographic location also at the entrance of the tunnel. Video 702 continues to show frames 3-6 as the video shows a biker moving through the tunnel. However, there may be no corresponding GPS data for geographic locations within the tunnel. This may be due to the GPS device recording the GPS data has no communication with the GPS satellite system orbiting overhead due to interference from being within the tunnel. Thus, based on the prior art techniques, the map view 704 may show the next frame (frame 3 730) corresponding to the next portion of geographic data in the GPS data file at the exit of the tunnel. Further, when the video 702 shows frame 4 712, the map view 704 shows frame 4 732 some distance from the exit of the tunnel. In addition, when the video 702 shows frame 5 714, the map view 704 shows frame 5 734 some further distance from the exit of the tunnel.

Consequently, frames 6-8 (716-720) are out of synchronization with frames 6-8 (736-740) of the map view 704. The video 702 and the map view 704 continue to be out of synchronization until a user can manually resynchronize the video 702 with the map view 704. This may be done by selecting further synchronization video frames and further synchronization map views then processing the timestamps of the further synchronization video frame and further synchronization portion of geographic data (corresponding to the further synchronization map view). However, this may be cumbersome and frustrating to the user as the video frame may be in an area with no further synchronization landmarks (the video file may be out of synchronization with the GPS data file showing a biker in the middle of a forest, on a mountain, down a remote rural road, etc.). Thus, the user may have to scan minutes if not hours of video file and map views to find a further synchronization landmark in both.

Alternatively, embodiments of the systems, devices, methods, and techniques of the present disclosure automatically synchronize 20-60 times per hour (after user selects a synchronization video frame and a synchronization portion of geographic information) to achieve a level of quality that is useful and enjoyable to a viewer presented with the synchronized video/GPS data. If a user were to use prior art techniques, the user would have to have to perform the tedious labor (several hours, in some instances) of manually synchronizing several video frames with portions of geographic data.

Figure 8:
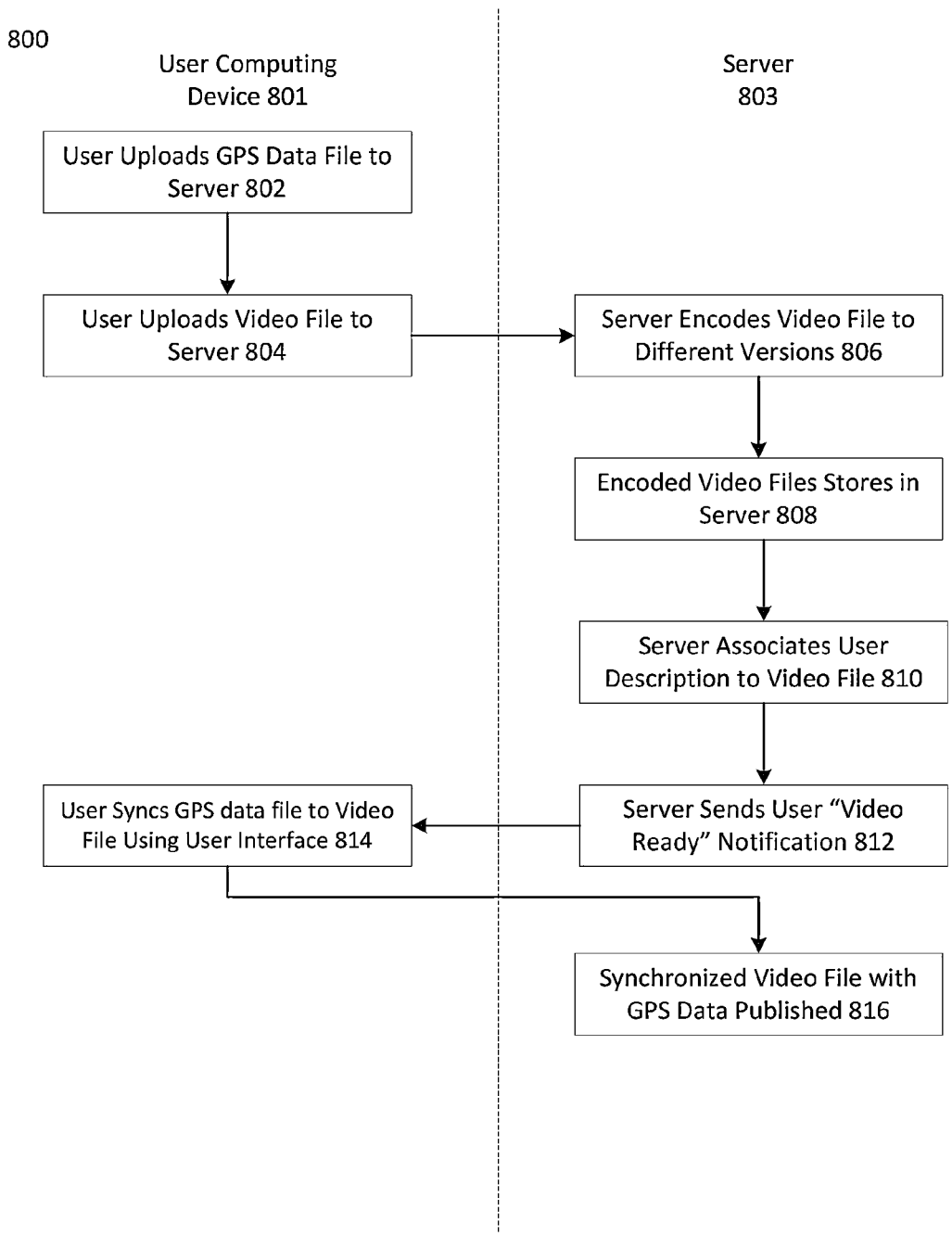
FIG. 8 is a flowchart of method of synchronizing uploaded video with map views based on GPS and performance data and presenting such synchronized video over the Internet to simulate outdoor athletic training in accordance with some embodiments.

FIG. 8 is a flowchart of method 800 of synchronizing uploaded video with map views based on GPS and performance data and presenting such synchronized video over the Internet to simulate outdoor athletic training in accordance with some embodiments. The method 800 includes a user uploading a GPS data file to a computer server 803 using a user computing device 801, as shown in block 802. The method 800 further includes the user uploading the video file to a computer server 803 using a user computing device, as shown in block 804. In addition, the method 800 includes the computer server 803 encoding the video file into difference versions/formats, as shown in block 806. For example, the computer server 803 may encode the video file in different formats so the video may be streamed, downloaded, or otherwise presented on a user computing device that may be a tablet computer, smartphone, and laptop computer. Further, the video file may be encoded in a format that is compatible with the operating system of the user computing device.

Moreover, the method 800 includes the computer server 803 stores the encoded video file in computer server 808. Further, the method 800 includes the computer server associating a user description to the video file 810. In addition, the computer server sends a user (to be viewed on the user interface on the user computing device) a "Video Ready" notification (e.g. via email, text, etc.), as shown in block 812. Moreover, the method 800 includes the computer server synchronizing GPS data to video file using a user interface using the techniques described herein, as shown in block 814. Further, the method 800 includes the synchronized video file with GPS data to be published on the computer server 803 to be accessed by other users/view, as shown in block 816.

Figure 9:
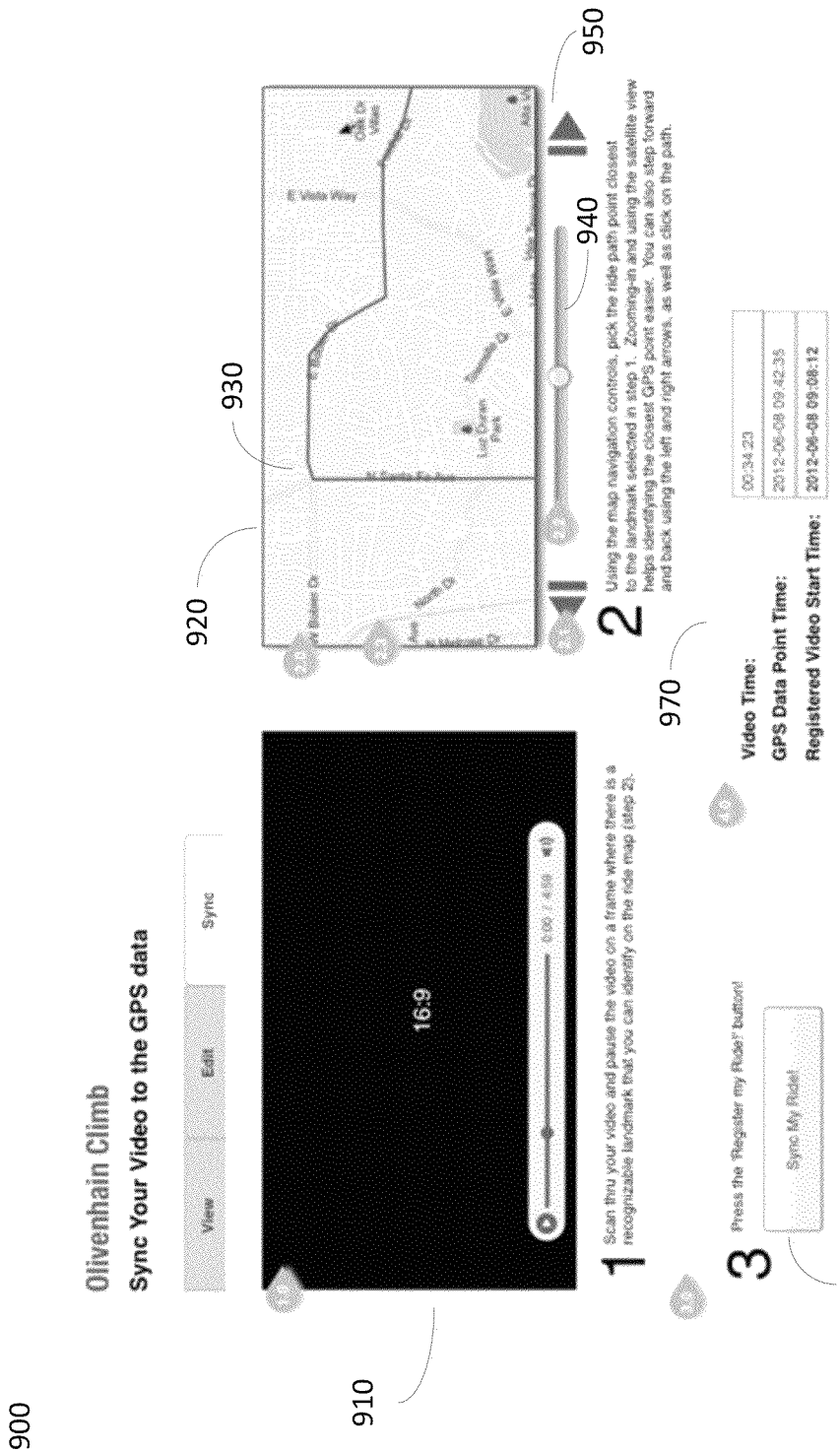
FIG. 9 is an example screenshot of a user interface used in synchronizing uploaded video with map views based on GPS and performance data in accordance with some embodiments.

FIG. 9 is an example screenshot 900 of a user interface used in synchronizing uploaded video with map views based on GPS and performance data. Further, the screenshot 900 shows a video 910 of the biker. A user can select a portion of the video to view using the video slider at the bottom of the video screen 910. The user may pause or stop the video at a frame showing a synchronization landmark. In addition, the map view 920 shows a map image of a geographic location corresponding to the frame shown in video 910. Users can manipulate the map view (zoom) to find a synchronization location using Forward and Back dialog boxes 950. In addition, the users use the "path slider" 940 which allows user to scan through the map views 920 to find a synchronization landmark. Further, a user clicking on a path data point 930 updates the timestamp as well as the position of the path slider. The user may stop or pause the video 910 on a synchronization video frame and the map view 920 on a synchronization map view such that a synchronization landmark is displayed on each. In addition, the user may click on a dialog box 960 to synchronize the uploaded video with the uploaded GPS and performance data based on the synchronization video frame and synchronization map view as described herein. That is, a computer server receives user input to determine a synchronization video frame and a synchronization map view (and synchronization portion of geographic data) to synchronize the video as described herein. Moreover, the screenshot 900 shows a timestamp display 970 that includes text field values that are automatically calculated based on the frame displayed in the video 910 and map view 920.

In some embodiments of the present disclosure, the user selected synchronization portion of geographic data may be part of the uploaded GPS/Performance data file. However, alternate embodiments allow for a user to select a synchronization portion of geographic data that is not part of the uploaded GPS/Performance data file. In such an embodiment, the video 910 may show a biker traveling a bike path based on an uploaded video. Further, the map view 920 shows a corresponding map view of the biker traveling the bike path based on an uploaded GPS/Performance data file. Further, the GPS data may record at different locations along the bike path. However, a user may like to synchronize the video based on a synchronization landmark not recorded in the GPS/Performance data file.

For example, the video 910 includes a bike path that runs north on Maple Street that crosses Oak Street, Elm Street, and Birch Street each street 150 meters apart from one another. The GPS/Performance data file recorded geographic data during the riding of the bike path at a location 10 meters south of the intersection of Maple Street and Oak Street, 5 meters south from the intersection of Maple Street and Elm Street and 15 meters north of the intersection of the Maple Street and Birch Street. The user may scan the video 910 until it a video frame shows the intersection of Maple Street and Elm Street. The map view 920 may show a continuous route of the bike path is running north on Maple Street crossing Oak Street, Elm Street, and Birch Street based on the uploaded GPS/Performance data file. Further, the user may select the intersection of Maple Street and Elm Street as the synchronization landmark. That is, the user adjusts the video 910 to show a frame presenting the intersection of Maple Street and Elm Street. Moreover, the user may select the intersection of Maple Street and Elm Street on map view 920. Note, the intersection of Maple Street and Elm Street is not part of the geographic data in the GPS/Performance data file. Thus, the user may select a synchronization landmark, hence a selected synchronization portion of geographic data corresponding to the synchronization landmark shown in the synchronization video frame that is not part of the geographic data in the GPS data file. The user may then synchronize 960 the video with the GPS data based on the selected synchronization video frame and selected synchronization portion of geographic data (e.g. intersection of Maple Street and Elm Street) not part of the GPS/Performance data file.

Further, a computer server receives and processes the selected synchronization video frame and the synchronization portion of geographic data. Such processing may include determining a portion of the geographic data that is part of the GPS/Performance data file nearest to the selected synchronization portion of geographic data. For example, the selected synchronization portion of geographic data is the intersection of the Maple Street and Elm Street. The computer server processes the GPS/Performance data to determine the portion of the geographic data that is part of the GPS/Performance data file nearest to the selected synchronization portion of geographic data. In such an example, such a portion of geographic data that is part of the GPS/Performance data file corresponds to 5 meters south of the intersection of Maple Street and Elm Street. Thus, the portion of the geographic data that is part of the GPS/Performance data file nearest to the selected synchronization portion of geographic data may be considered/designated to be corresponding to the synchronization video frame. In addition, the computer server may determine the timestamp of the portion of geographic data corresponding to the synchronization video frame. Moreover, the computer server may use the timestamp of the synchronization video frame as well as the timestamp of the portion of geographic data corresponding to the synchronization video frame to synchronize the uploaded video with the uploaded GPS/Performance data file (using techniques described in the present disclosure).

In an additional embodiment, the computer server may extrapolate the timestamp of selected synchronization portion of geographic data based on timestamps of two nearest/neighboring portions of geographic data that are part of the GPS/Performance data. For example, the computer server may determine the timestamp of the portion of geographic data associated with location 5 meters south of the intersection of Maple Street and Elm Street as well as the timestamp of the portion of geographic data associated with location 15 meters north of the intersection of Maple Street and Birch Street. The computer server may calculate the speed of the biker based on the geographic data and timestamps corresponding to each location and then extrapolate/determine the timestamp of the selected synchronization portion of geographic data (e.g. intersection of Maple and Elm Street). Thus, the selected synchronization portion of geographic data may be considered/designated to correspond to the synchronization video frame. Further, the computer server may then synchronize the uploaded video based on the timestamp of the selected synchronization video frame and the selected synchronization portion of geographic data (using the techniques described in the pending disclosure).

Figure 10:
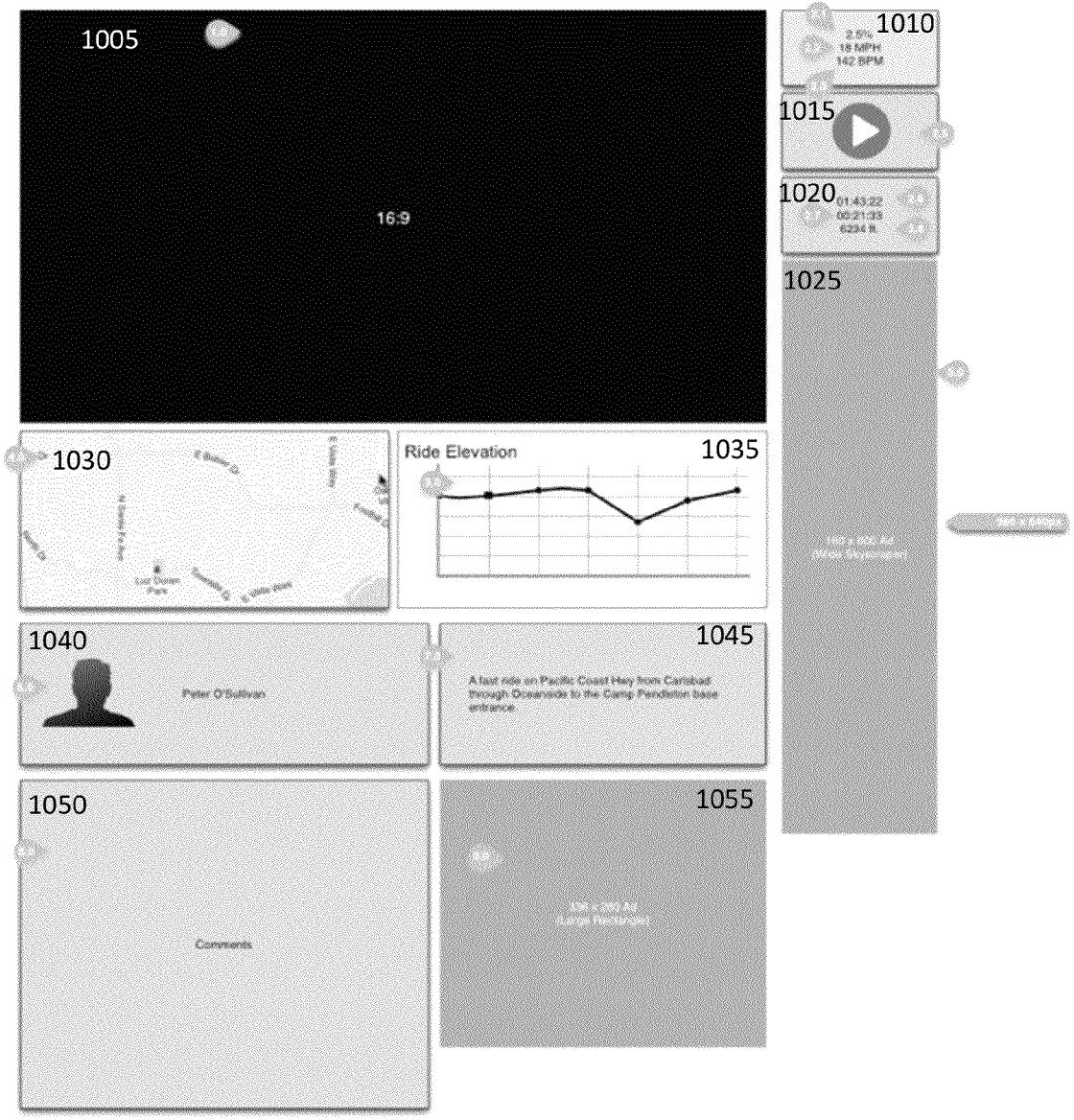
FIG. 10 is an example screenshot of a user interface used in presenting synchronized video with map views based on GPS and performance data over the Internet to simulate outdoor athletic training in accordance with some embodiments.

FIG. 10 is an example screenshot 1000 of a user interface used in presenting synchronized video with map views based on GPS and performance data over the Internet to simulate outdoor athletic training in accordance with some embodiments. The screenshot 1000 may be a webpage that is part of a website hosted by a remote computer server and provided to a user computing device on a user interface (e.g. web browser) over the Internet. The website may allow for user to crowd source videos to be viewed by other users to simulate outdoor training in an indoor environment.

Further, the screenshot 1000 includes a video 1005 of a bike ride as well as the map view 1030. The video 1005 is synchronized with the map views 1030 and presented to a viewer using the techniques described herein. Further, the screenshot 1000 includes a ride metrics dashboard 1010 that displays the incline of the road in which the biker is riding, the speed of the biker, and the heart rate of the biker. Such displayed data is processed from the GPS data and performance data uploaded by a user. In some embodiments, the dashboard may include the distanced traveled by the biker. Further, the screenshot 1000 may include a pause/play button 1015 for the video 1015 and map view 1030. A further ride metrics dashboard 1020 may include the current ride time of the video 1005, the time left for the video 1005, and the current elevation of the biker.

A user may be viewing (e.g. viewer) the video 1005, map views 1030 and ride metrics (1010, 1020) on a table computer while riding an indoor exercise bike. Such a user/viewer may desire to simulate an outdoor training environment. Thus, if the video 1005, map views 1030, and (1010, 1020) show that the bike ride is traveling up an incline, the user/viewer may adjust the incline or resistance of the exercise bike to match the displayed ride metrics (1010, 1020). Alternatively, if video 1005, map views 1030, and (1010, 1020) show that the bike ride is traveling down a level road at 10 miles/hour, the user/viewer may adjust the incline or resistance of the exercise bike and pace his pedaling to match the displayed ride metrics (1010, 1020).

Further embodiments, may use other exercise equipment while viewing synchronized videos/GPS/Performance data such as a stair climber, treadmill or other stationary exercise machine. Such synchronized videos/GPS/Performance data may be of biking, walking, running, hiking trails or of any other outdoor activity to simulate outdoor exercise, training, or recreational activity. In additional embodiments, the exercise equipment may have electronically configurable components to adjust the incline, resistance, etc. of the exercise equipment. Such embodiments may have application programmable interfaces (APIs) that allow a computer server with uploaded GPS/Performance data transmit the GPS/Performance data to the exercise equipment to adjust the incline, resistance, etc. of the exercise equipment based on the GPS/Performance data.

In addition, the screenshot 1000 includes a ride profile/elevation graph that graphically shows the elevation of the bike ride shown in video 1005. The screenshot 1000 also includes space for an advertising block 1025 to provide revenue for the website. Further, the screenshot 1000 includes data 1040 of the user who uploaded the video 1005 (e.g. crowd source contributor). Moreover, the screenshot 1000 includes a ride description 1045 as submitted by the crowd source contributor. For example, Peter, a crowd source contributor/user, uploaded the ride shown in video 1005. Further, Peter, the crowd source contributor, provides a description of the ride such as a Pacific Coast Highway bike ride from Carlsbad to Camp Pendleton. In addition, the screenshot 1000 includes a comments section 1050 that allows user who have viewed (or uploaded) the video 1005 to provide comments regarding the video 1005. For example, the a viewer/user may ask whether Peter, the crowd source contributor can take video of a certain bike trail, and the comments section 1050 may allow Peter, the crowd source contributor to respond. In addition, the screenshot 1000 includes another advertising block 1055 to provide additional revenue for the website.

In the foregoing specification, specific embodiments have been described. However, one of ordinary skill in the art appreciates that various modifications and changes can be made without departing from the scope of the invention as set forth in the claims below. Accordingly, the specification and figures are to be regarded in an illustrative rather than a restrictive sense, and all such modifications are intended to be included within the scope of present teachings.

The benefits, advantages, solutions to problems, and any element(s) that may cause any benefit, advantage, or solution to occur or become more pronounced are not to be construed as a critical, required, or essential features or elements of any or all the claims. The invention is defined solely by the appended claims including any amendments made during the pendency of this application and all equivalents of those claims as issued.

Moreover in this document, relational terms such as first and second, top and bottom, and the like may be used solely to distinguish one entity or action from another entity or action without necessarily requiring or implying any actual such relationship or order between such entities or actions. The terms "comprises," "comprising," "has", "having," "includes", "including," "contains", "containing" or any other variation thereof, are intended to cover a non-exclusive inclusion, such that a process, method, article, or apparatus that comprises, has, includes, contains a list of elements does not include only those elements but may include other elements not expressly listed or inherent to such process, method, article, or apparatus. An element proceeded by "comprises . . . a", "has . . . a", "includes . . . a", "contains . . . a" does not, without more constraints, preclude the existence of additional identical elements in the process, method, article, or apparatus that comprises, has, includes, contains the element. The terms "a" and "an" are defined as one or more unless explicitly stated otherwise herein. The terms "substantially", "essentially", "approximately", "about" or any other version thereof, are defined as being close to as understood by one of ordinary skill in the art, and in one non-limiting embodiment the term is defined to be within 10%, in another embodiment within 5%, in another embodiment within 1% and in another embodiment within 0.5%. The term "coupled" as used herein is defined as connected, although not necessarily directly and not necessarily mechanically. A device or structure that is "configured" in a certain way is configured in at least that way, but may also be configured in ways that are not listed.

It will be appreciated that some embodiments may be comprised of one or more generic or specialized processors (or "processing devices") such as microprocessors, digital signal processors, customized processors and field programmable gate arrays (FPGAs) and unique stored program instructions (including both software and firmware) that control the one or more processors to implement, in conjunction with certain non-processor circuits, some, most, or all of the functions of the method and/or apparatus described herein. Alternatively, some or all functions could be implemented by a state machine that has no stored program instructions, or in one or more application specific integrated circuits (ASICs), in which each function or some combinations of certain of the functions are implemented as custom logic. Of course, a combination of the two approaches could be used.

Moreover, an embodiment can be implemented as a computer-readable storage medium having computer readable code stored thereon for programming a computer (e.g., comprising a processor) to perform a method as described and claimed herein. Examples of such computer-readable storage mediums include, but are not limited to, a hard disk, a CD-ROM, an optical storage device, a magnetic storage device, a ROM (Read Only Memory), a PROM (Programmable Read Only Memory), an EPROM (Erasable Programmable Read Only Memory), an EEPROM (Electrically Erasable Programmable Read Only Memory) and a Flash memory. Further, it is expected that one of ordinary skill, notwithstanding possibly significant effort and many design choices motivated by, for example, available time, current technology, and economic considerations, when guided by the concepts and principles disclosed herein will be readily capable of generating such software instructions and programs and ICs with minimal experimentation.

The Abstract of the Disclosure is provided to allow the reader to quickly ascertain the nature of the technical disclosure. It is submitted with the understanding that it will not be used to interpret or limit the scope or meaning of the claims. In addition, in the foregoing Detailed Description, it can be seen that various features are grouped together in various embodiments for the purpose of streamlining the disclosure. This method of disclosure is not to be interpreted as reflecting an intention that the claimed embodiments require more features than are expressly recited in each claim. Rather, as the following claims reflect, inventive subject matter lies in less than all features of a single disclosed embodiment. Thus the following claims are hereby incorporated into the Detailed Description, with each claim standing on its own as a separately claimed subject matter.

We claim:

1. An automatic video presentation method for real-time matching of GPS information with a non-GPS video, comprising:
   receiving, by a computer server over a communication network, a streaming video file from another system, wherein the video file includes one or more video frames each video frame having a video timestamp;
   receiving a global positioning system (GPS) data file and hosted on the computer server, the GPS data file including one or more portions of geographic data each portion of geographic data having a timestamp;
   presenting, via the computer server, a video frame selection window to a user for user selection of a time synchronization video frame;
   receiving, by the computer server, the user selection of a time synchronization video frame;
   presenting, via the computer server, a geographic map and selection window to the user for user selection of a corresponding geographic (GPS based) location of the user selected time synchronization video frame;
   receiving, by the computer server, the user selection of the corresponding (GPS based) geographic location data;
   processing, by the computer server, the selected synchronization video frame and the synchronization portion of geographic (GPS based) location data to determine the timestamp of the synchronization video frame and the timestamp of a portion of the geographic (GPS based) location data corresponding to the synchronization video frame; and
   synchronizing in a continuous fashion subsequent time stamps of the streamed video file to the GPS data file, by the computer server, the GPS data file with the video file based on the timestamp of the continuously synchronized video frame and the timestamp of the user selected geographic data corresponding to the synchronization video frame.

2. The method of claim 1, further comprising modifying a length of the GPS data file based on synchronizing the GPS data file with the video file.

3. The method of claim 1, wherein the synchronization portion of geographic data is one of the one or more portions of the geographic data.

4. The method of claim 1, further comprising generating a notification after the video file and GPS data file is received.

5. The method of claim 1, further comprising synchronizing performance data associated with at least one of skiing, snowboarding, snowmobiling, off-terrain vehicle riding, running, hiking, walking, any outdoor activity, and heart rate information, with the video file, the GPS data including performance data having one or more portions of performance data, each portion of performance data having a timestamp.

6. The method of claim 1, wherein synchronization video frame displays a synchronization landmark and the synchronization portion of geographic data includes geographic information relating to the synchronization landmark.

7. The method of claim 1, further comprising providing the synchronized video file with one or more map views based on the GPS data file to one or more viewing user devices over the communication network.

8. The method of claim 7, wherein providing the synchronized video file with the GPS data file to one or more viewing user devices includes:
    processing a currently playing video frame to determine a video playback timestamp relative to a video duration;
    calculating the video current timestamp based on the video playback timestamp and an absolute video start timestamp;
    processing the GPS data file to determine a GPS current timestamp corresponding to a current portion of the geographic data that is closest to the video current timestamp;
    displaying a video frame corresponding to the video current timestamp and a map view based on the portion of geographic data having the GPS current timestamp.

9. The method of claim 1, wherein the synchronization of the video file with the GPS data file includes:
    processing, by the computer server, the synchronization video frame to determine a relative timestamp of the synchronization video frame;
    processing the synchronization portion of the geographic data to determine an absolute timestamp of the synchronization portion of the geographic data;
    processing the video file to determine a duration of the video file;
    calculating an absolute video start timestamp based on the absolute time stamp of the synchronization portion of the geographic data and the relative timestamp of the synchronization video frame;
    calculating an absolute video end timestamp based on the absolute video start timestamp and the video duration.

10. The method of claim 1, wherein the streamed video file and GPS file are not pre-processed prior to synchronization.

11. A device for automatic video presentation of real-time matching of GPS information with non-GPS video, comprising:
    a storage device;
    one or more processors coupled to the storage device, the one or more processors configured to:
        receive over a communication network and store in the storage device, a streaming video file from another system, wherein the video file includes one or more video frames each video frame having a video timestamp, and a global positioning system (GPS) data file, the GPS data file including one or more portions of geographic data each portion of geographic data having a timestamp;
        present a video frame selection window to a user for user selection of a time synchronization video frame;
        receive video user input from a user device indicating the user selection of a synchronization video frame that is one of the one or more video frames of the video file;
        present a geographic map and selection window to the user for user selection of a corresponding geographic (GPS based) location of the user selected time synchronization video frame;
        receive, over the communication network, GPS user input from the user device indicating a user selection of a synchronization portion of geographic data;
        process the selected synchronization video frame and the synchronization portion of geographic data to determine the timestamp of the synchronization video frame and the timestamp of a portion of the geographic data; and
        synchronize in a continuous fashion the GPS data file with the video file based on the timestamp of the synchronization video frame and the timestamp of the portion of the geographic data corresponding to the synchronization video frame.

12. The device of claim 11, wherein the one or more processors are further configured to modify a length of the GPS data file based on synchronizing the GPS data file with the video file.

13. The device of claim 11, wherein synchronization portion of geographic data is one of the one or more portions of the geographic data.

14. The device of claim 11, wherein the one or more processors are further configured to generate a notification after the video file and GPS data file is received.

15. The device of claim 11, wherein the one or more processors are further configured to synchronize performance data associated with at least one of skiing, snowboarding, snowmobiling, off-terrain vehicle riding, running, hiking, walking, any outdoor activity, and heart rate information with the video file, the GPS data including performance data having one or more portions of performance data, each portion of performance data having a timestamp.

16. The device of claim 11, wherein synchronization video frame displays a synchronization landmark and the synchronization portion of geographic data includes geographic information relating to the synchronization landmark.

17. The device of claim 11, wherein the one or more processors are further configured to provide the synchronized video file with one or more map views based on the GPS data file to one or more viewing user devices over the communication network.

18. The device of claim 17, wherein providing the synchronized video file with the GPS data file to one or more viewing user devices includes:
    processing a currently playing video frame to determine a video playback timestamp relative to a video duration;
    calculating the video current timestamp based on the video playback timestamp and an absolute video start timestamp;
    processing the GPS data file to determine a GPS current timestamp corresponding to a current portion of the geographic data that is closest to the video current timestamp;
    displaying a video frame corresponding to the video current timestamp and a map view based on the a portion of geographic data having the GPS current timestamp.

19. The device of claim 11, wherein synchronization of the video file with the GPS data file includes:
    processing, by the computer server, the synchronization video frame to determine a relative timestamp of the synchronization video frame;

processing the synchronization portion of the geographic data to determine an absolute timestamp of the synchronization portion of the geographic data;
processing the video file to determine a duration of the video file;
calculating an absolute video start timestamp based on the absolute time stamp of the synchronization portion of the geographic data and the relative timestamp of the synchronization video frame;
calculating an absolute video end timestamp based on the absolute video start timestamp and the video duration.

20. An article of manufacture including computer readable media with instructions encoded and stored thereon, the stored instructions, when executed causes a processor to perform the steps of:
receiving, over a communication network, a streaming video file from another system, wherein the video file includes one or more video frames each video frame having a video timestamp;
receiving a global positioning system (GPS) data file, and hosted on the computer server, the GPS data file including one or more portions of geographic data each portion of geographic data having a timestamp;
presenting, via the computer server, a video frame selection window to a user for user selection of a time synchronization video frame;
receiving, over the communication network, a user selection of a time synchronization video frame;
presenting, via the computer server, a geographic map selection window to the user for user selection of a corresponding geographic (GPS based) location of the user selected time synchronization video frame;
receiving a user selection of the corresponding (GPS) geographic location data;
processing the selected synchronization video frame and the synchronization portion of geographic data to determine the timestamp of the synchronization video frame and the timestamp of a portion of the geographic (GPS based) location data corresponding to the synchronization video frame; and
synchronizing in a continuous fashion subsequent time stamps of the GPS data file with the video file based on the timestamp of the synchronization video frame and the timestamp of the user selected geographic data corresponding to the synchronization video frame.

* * * * *